(12) United States Patent
Mertens et al.

(10) Patent No.: US 6,284,871 B1
(45) Date of Patent: Sep. 4, 2001

(54) FACTOR IX BINDING PEPTIDES, DERIVED FROM FACTOR VIII AND THEIR USE AS INHIBITORS OF BLOOD COAGULATION

(75) Inventors: Koenraad Mertens, Leiden; Petrus Johannes Lenting, Amsterdam, both of (NL)

(73) Assignee: Stiching Centraal Laboratorium van de Bloedtransfusiedienst van Nederlandse Rode Kruis, Amsterdam (NL)

( * ) Notice: Subject to any disclaimer, the term of this patent is extended or adjusted under 35 U.S.C. 154(b) by 0 days.

(21) Appl. No.: 08/973,801

(22) PCT Filed: Jun. 12, 1996

(86) PCT No.: PCT/NL96/00236

§ 371 Date: Dec. 9, 1997

§ 102(e) Date: Dec. 9, 1997

(87) PCT Pub. No.: WO96/41816

PCT Pub. Date: Dec. 27, 1996

(30) Foreign Application Priority Data

Jun. 12, 1995 (EP) .................................................. 95201554

(51) Int. Cl.$^7$ ............................ A61K 35/14; C07K 17/00
(52) U.S. Cl. .......................... 530/383; 530/324; 530/328; 530/384; 530/829; 530/830; 514/2; 514/12; 514/16; 514/802; 514/834; 424/529; 424/532
(58) Field of Search ................................... 530/383, 384, 530/324, 328, 829, 830; 514/2, 12, 16, 802, 834; 424/529, 532

(56) References Cited

U.S. PATENT DOCUMENTS

| | | | |
|---|---|---|---|
| 4,885,277 | * 12/1989 | Nawroth et al. | 514/15 |
| 5,187,155 | * 2/1993 | Fair | 514/12 |

FOREIGN PATENT DOCUMENTS

| | | |
|---|---|---|
| WO 90/15615 | 12/1990 | (WO) . |
| WO 96/02572 | 2/1996 | (WO) . |
| WO 97/40145 | * 10/1997 | (WO) . |

OTHER PUBLICATIONS

Lenting et al., *The Journal of Biological Chemistry*, vol. 269, No. 10, pp. 7150–7155, Mar. 11, 1994.*
Gitschier et al., *Nature*, vol. 312, pp. 326–330, Nov. 22, 1984.*
Wood et al., *Nature*, vol. 312, pp. 330–337, Nov. 22, 1984.*
Toole et al., *Nature*, vol. 312, pp. 342–347, Nov. 22, 1984.*
Eaton et al., *Biochemistry*, vol. 25, pp. 505–512, 1986.*
Leuting et al., *The Journal of Biological Chemistry*, vol. 270, No. 22, pp. 14884–14890, Jun. 23, 1995.*
Leuting et al., *The Journal of Biological Chemistry*, vol. 271, No. 41, pp. 25332–25337, Oct. 11, 1996.*
P.J. Lenting et al, "The Sequence Glu$^{1811}$–Lys$^{1818}$ of Human Blood Coagulation Factor VIII Comprises a Binding Site for Activated Factor IX", *The Journal of Biological Chemistry*, vol. 271, No. 4, Jan. 26, 1996, pp. 1935–1940.
P.J. Lenting et al, "Identification of a Binding Site for Blood Coagulation Factor IXa on the Light Chain of Human Factor VIII", *The Journal of Biological Chemistry*, vol. 269, No. 10, Mar. 11, 1994, pp. 7150–7155.
J.W. Van de Loo et al, "Research Reports: Theme I Hemostasis and Thrombosis—Identification and Characteristics of the Binding Site of a Murine Monoclonal Antibody That Inhibits Factor–VIII Function", *Annual Report Dr. Karl Landsteiner Foundation*, Amsterdam Netherlands, p. 1–2 (1992).
G.A. Vehar et al, "Structure of Human Factor VIII", *Nature*, vol. 312, No. 5992, Nov.–Dec. 1984, pp. 337–342.
F.J. Walker et al, "Identification of the Binding Site for Activated Protein C on the Light Chain of Factors V and VIII", *The Journal of Biological Chemistry*, vol. 265, No. 3, Jan. 25, 1990, pp. 1484–1489.

* cited by examiner

Primary Examiner—Christopher S. F. Low
Assistant Examiner—Abdel A. Mohamed
(74) Attorney, Agent, or Firm—Hoffman & Baron, LLP (57) ABSTRACT

The present invention relates to biologically active peptides which specifically inhibit the Factor IX-dependent pathway of blood coagulation. These peptides are based on a specific motif which represents a sequence of Factor VIII (amino acid 1811–1818) involved in binding to activated Factor IX as well as to the intact Factor IX zymogen. Binding of said peptides to Factor IX or activated derivatives thereof effectively inhibits complex assembly with Factor VIII. These peptides thereby specifically interfere in the Factor IX-dependent pathway of thrombin formation, while leaving other haemostatic pathways unaffected. By virtue of this unique specificity, the peptides of this invention are particularly useful in novel pharmaceutical compositions for the treatment of thrombotic disorders.

12 Claims, 5 Drawing Sheets

Primary Structure

I   FYSSLISYEEDQRQGAEPRKNFVKPNETKTYFWKVQHHMAPTKDEFDCKAWAYF

II  TKSWYFTENMERNCRAPCNIQMEDPTFKENYRFHAIN

III HFSGHVFTVRKKEEYKMALYNL

FACTOR IX BINDING PEPTIDES, DERIVED FROM FACTOR VIII AND THEIR USE AS INHIBITORS OF BLOOD COAGULATION

FIELD OF THE INVENTION

The present invention relates to methods for the preparation of highly specific anticoagulants which can be used in therapeutic compositions for the treatment of thrombosis. The biologically active ingredient of said preparations comprises one or more peptides that selectively inhibit the Factor IX-dependent coagulation pathway. This invention provides methods for obtaining such peptides, and for their formulation into pharmaceutical compositions with antithrombotic activity.

BACKGROUND OF THE INVENTION

The arrest of bleeding involves the concerted action of various haemostatic pathways, which eventually lead to thrombus formation. Thrombi are depositions of blood constituents on the surface of the vessel wall, and are mainly composed of aggregated blood platelets and insoluble, cross-linked fibrin. Fibrin formation occurs by limited proteolysis of fibrinogen by thrombin. This enzyme is the final product of the coagulation cascade, a sequence of zymogen activations which occur at the surface of activated platelets and leukocytes, and of a variety of vascular cells (for review see K. G. Mann et al., *Blood* vol 76, 1990, pp 1–16).

Normally thrombus formation remains localized at sites of vascular injury, since platelet aggregation and adhesion is mediated by agonists associated with the growing thrombus, such as locally formed thrombin. Under certain pathological conditions however, the formation of these depositions does not remain limited to the site of injury. Thrombi then may occur in arteries and veins anywhere in the circulation, which may ultimately result in vessel obstruction and blood flow arrest. This provides the mechanism underlying a variety of thrombotic disorders, including deep vein thrombosis, pulmonary embolism, disseminated intravascular coagulation, peripheral arterial disease, myocardial infarction and stroke (J. F. Mustard et al., in: A. L. Bloom and D. P. Thomas (Eds.), *Haemostasis and Thrombosis*, 2nd edition, Churchill-Livingstone, Edinburgh, 1987, pp 503–526).

Figure 1:
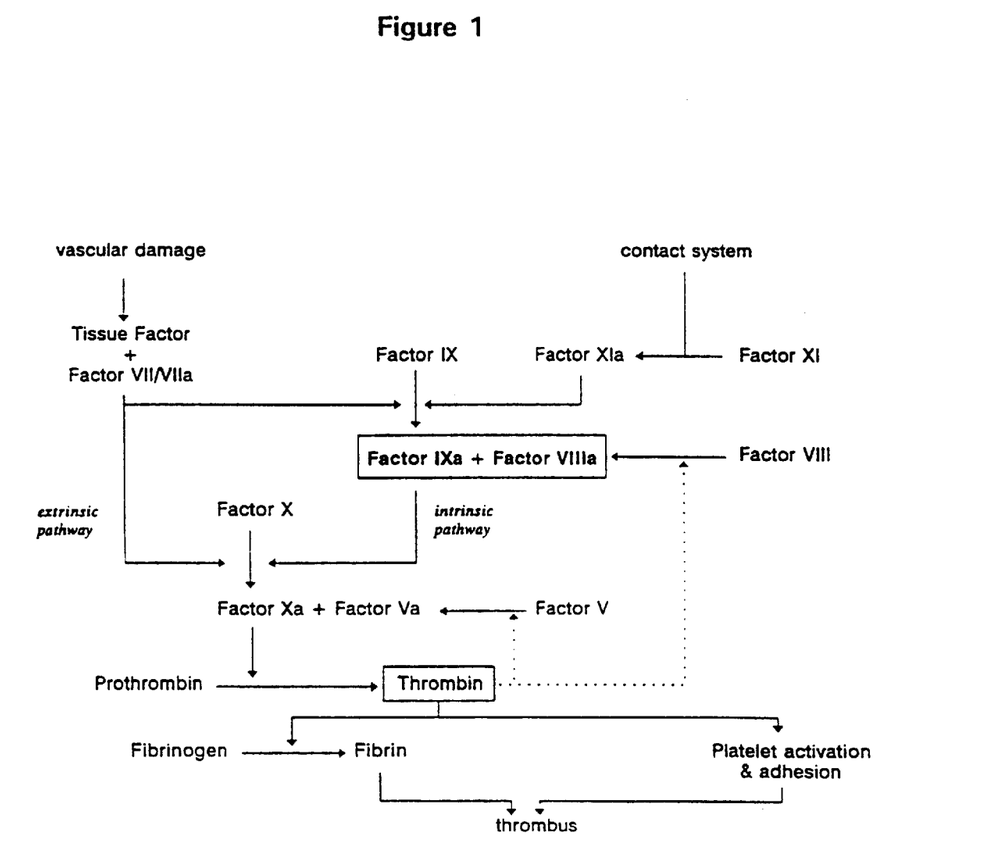

Numerous strategies have been developed for the treatment of thrombotic disorders. These antithrombotic therapies have in common that they are based on interference in the haemostatic system. This approach carries the inherent risk of bleeding, since the haemostatic system is no longer fully responsive to potential injury. Therefore, antithrombotic benefits are inevitably associated with antihaemostatic risks. In attempts to improve the benefit-to-risk ratio, novel antithrombotic agents are continuously being developed. The various antithrombotic strategies have been extensively reviewed elsewhere, and some are briefly summarized below to illustrate the various developments in this field. These include:

(a) General inhibitors of thrombin formation. One well established strategy consists of oral anticoagulant therapy employing vitamin K antagonists. This interferes in the biosynthesis of the so-called vitamin K-dependent coagulation factors, which include Factors VII, IX, X and prothrombin. This therapy thus is aspecific, as it affects both the extrinsic and the intrinsic coagulation pathway (see FIG. 1). Although widely used, oral anticoagulation requires intensive monitoring in order to reduce the bleeding risk associated with this therapy (see J. Hirsh et al., in: R. W. Colman et al. (Eds.), *Hemostasis and Thrombosis, Basic Principles and Clinical Practice*, 3rd edition, Lippincott, Philadelphia, 1994, pp 1567–1583). A similarly aspecific therapy consists of the administration of heparin. This compound accelerates the inactivation of a number of components, including thrombin and the activated forms of Factors IX and X (Factors IXa and Xa), by their natural inhibitor Antithrombin III. Over the past two decades, low molecular weight derivatives of heparin, which display an increased specificity for Factor Xa over thrombin inhibition, have been developed in an attempt to reduce the bleeding risk associated this therapy (see T. W. Barrowcliffe and D. P. Thomas, in: A. L. Bloom et al. (Eds.), *Haemostasis and Thrombosis*, 3rd edition, Churchill-Livingstone, Edinburgh, 1994, pp 1417–1438).

(b) Specific thrombin inhibitors. As thrombin is the key enzyme in platelet activation, fibrin formation, and activation of the cofactors Factors V and VIII (see FIG. 1), it may seem an attractive target for antithrombotic therapy. Numerous studies have been devoted to the small leech protein called hirudin, and to peptides derived thereof (J. M. Maraganore, *Thromb. Haemostasis* vol 70, 1993, pp 208–211). Although these components are more effective than for instance heparin in animal models of experimental thrombosis, clinical trials initially revealed an unexpectedly high frequency of bleeding, demonstrating that the thrombin-directed approach may produce a significant antihaemostatic effect, with a relatively unfavorable benefit-to-risk ratio (L. A. Harker, *Biomedical Progress* vol 8, 1995, 17–26).

(c) Specific Factor Xa inhibitors. Suppression of thrombin formation can effectively be achieved by inhibiting Factor Xa, which is the prothrombin activating enzyme in the coagulation cascade (see FIG. 1). Theoretically, this has the advantage of inhibiting vascular thrombus formation while still permitting a small, but haemostatically important amount of thrombin to be produced. Two naturally occurring peptide inhibitors of Factor Xa have recently been developed, the tick anticoagulant peptide (G. P. Vlasuk, *Thromb. Haemostasis* vol 70, 1993, pp 212–216) and antistasin, a leech anticoagulant (G. P. Tuszynsky et al., *J. Biol. Chem.* vol 262, 1987, pp 9718–9723). These polypeptides, and various oligopeptide derivatives thereof (N. Ohta et al., *Thromb, Haemostasis* vol 72, 1994, pp 825–830) may provide a more favorable benefit-to-risk ratio than agents with a broader specificity.

(d) Inhibitors of platelet activation and adhesion. Numerous studies have addressed this strategy, which has the theoretical advantage of specifically interrupting thrombin-dependent platelet recruitment at sites of vascular injury, while sparing the production of fibrin (see L. A. Harker et al., in: R. W. Colman et al. (Eds.), *Hemostasis and Thrombosis, Basic Principles and Clinical Practice*, 3rd edition, Lippincott, Philadelphia, 1994, pp 1638–1660). This strategy can be accomplished by various agents, including synthetic thrombin receptor antagonists, or monoclonal antibodies or peptides that interfere in the adhesion process. Although this approach seems particularly useful in arterial thrombosis, bleeding episodes still have been reported, suggesting that the specificity of this strategy may not have satisfactorily eliminated the antihaemostatic risk.

In summary, evaluation of current antithrombotic strategies in terms of antithrombotic benefits versus antihaemostatic risks reveals that the benefit-to risk ratio tends to be more favorable for strategies that interfere in one specific step rather than in a more general phase of the haemostatic system (L. A. Harker, *Biomedical Progress* vol 8, 1995, 17–26). Although the development of inhibitors specific for Factor Xa seems to be a promising improvement, this approach still blocks the common (intrinsic and extrinsic) pathway of thrombin generation (see FIG. 1), and thereby thrombin-dependent platelet activation as well. An urgent need therefore exists for more specific anti-thrombotic agents that inhibit one single haemostatic pathway, while leaving other pathways unaffected.

More selective inhibition of the haemostatic system should be achievable if agents would exist that exclusively interfere in the intrinsic pathway of Factor X activation. This would leave the extrinsic pathway intact, allowing the formation of small, but haemostatically important amounts of Factor Xa and thrombin. While the formation of the platelet plug associated with the initial phase of bleeding arrest thus would remain unaffected, the formation of larger amounts of thrombin and fibrin would be suppressed (see FIG. 1). A potentially successful strategy for achieving selective inhibition of the intrinsic coagulation pathway may consist of employing Factor VIII as a template for designing antagonist peptides which counteract its biological function. One attempt has been described which utilizes synthetic peptides mimicking the phospholipid-binding domain of Factor VIII (T. S. Zimmerman et al., International Patent Application, WO 90/15615, published Dec. 27, 1990). This region, which is located at the utmost C-terminus of the Factor VIII protein (the so-called C2-domain, see below), comprises a sequence that binds to specific phospholipids (phosphatidylserine) on the surface of activated platelets, leukocytes or vascular cells (P. A. Foster et al., *Blood* vol 75, 1990, pp 1999–2004). These phospholipid-binding peptides impede Factor VIII from participating in the blood coagulation process and as such may act as anticoagulants. However, because coagulation factors other than Factor VIII, including Factor V, Factor VII, Factor IX, Factor X and prothrombin (see FIG. 1) share the same requirement for phosphatidylserine-containing membranes (see K. G. Mann et al., *Blood* vol 76, 1990, pp 1–16), these phospholipid-binding peptides affect multiple steps in the coagulation system. Therefore, this approach lacks the desired specificity for the intrinsic coagulation pathway. Such selective inhibition should be achievable by using compounds which interfere in Factor VIII-Factor IX interaction, for instance by blocking the Factor VIII binding site on Factor IXa immediately after its formation during the haemostatic response. It would be even more preferable if such compounds would block the Factor VIII binding site on Factor IX prior to its conversion into Factor IXa, thus allowing prophylactic application as well. The design of such agents, however, until now has been hampered by a lack of knowledge concerning the molecular sites involved in Factor VIII(a)-Factor IX(a) interaction.

With regard to the binding sites involved in the interaction between Factors VIII and IX, only a few reports have been published so far. These have focused on Factor VIII, which is the cofactor of Factor IXa in the Factor X activating complex (see FIG. 1). Factor VIII is synthesized as a single chain polypeptide of 2332 amino acids, with the typical domain structure A1-A2-B-A3-C1-C2 (G. A. Vehar et al., *Nature* vol 312, 1984, pp 337–342; J. J Toole et al., *Nature* vol 312, 1984, 342–347). Due to endoproteolytic processing, Factor VIII circulates in plasma as a heterodimeric complex of heavy and light chain. The light chain comprises amino acid residues 1649–2332, and contains the A3-C1-C2 domains. The heavy chain contains the domains A1-A2-B (residues 1–1648) and is heterogeneous due to limited proteolysis at a number of positions within the B-domain. Lenting et al. (*J. Biol. Chem.* vol 269, 1994, pp 7150–7155) have reported that Factor IXa specifically binds to the light chain of Factor VIII. Subsequently, the same investigators have reported similar studies employing Factor VIII light chain cleavage products, and concluded that the Factor IXa binding site should be located between residues 1722 and 2332 on the Factor VIII light chain (M. J. S. H. Donath et al., *J. Biol. Chem.* vol 270, 1995, pp 3648–3655). It has further been observed that the interaction between Factor IXa and Factor VIII light chain is inhibited by a monoclonal antibody, designated CLB-CAg A, which is directed against the Factor VIII A3-domain (P. J. Lenting et al., *J. Biol. Chem.* vol 269, 1994, pp 7150–7155), and more specifically against a region spanning the residues 1801–1823 (J. W. van de Loo et al., Annual Report 1992, Dr. Karl Landsteiner Foundation, Amsterdam, p 1).

Although these observations suggest that the Factor VIII A3-domain contributes to Factor IXa binding, other investigators have disclosed data that teach away from the Factor VIII light chain being a significant Factor IXa binding region. Fulcher et al. (Scientific Report 1992–1993, Scripps Research Institute, La Jolla, U.S.A., p 159) reported that a monoclonal antibody against the Factor VIII heavy chain region 701–750, or synthetic peptides derived from residues 698–710 or 698–712, inhibit Factor IXa-dependent functional assays. The same study reports that these peptides directly interact with Factor IXa, thus supporting the concept that the Factor VIII A2-domain region 698–710 represents a functionally important Factor IXa binding site (J. I. Jorquera et al., *Circulation* vol 86, 1992, p 685). Additional evidence for involvement of the Factor VIII heavy chain A2-domain in Factor IXa binding, albeit at a different site, has been reported by other investigators (P. J. Fay et al., *J. Biol. Chem.* vol 269, 1994, p 20522–20527). In the latter study, a synthetic peptide corresponding to the A2-domain residues 558–565 has been employed to identify this region as a Factor IXa interactive site.

In summary, a number of potential Factor IXa binding sites have been identified: at least two distinct sites within the A2-domain on the Factor VIII heavy chain, and one or more additional sites on the Factor VIII light chain region 1722–2332, presumably within the A3-domain. These divergent data imply that either multiple sites exist which are involved in Factor VIII binding, or that multiple sequences contribute to the formation of one single Factor IXa binding site. Thus, it remains difficult to conclusively identify a predominant site as appropriate template for the design of effective antihaemostatic agents. Moreover, prior disclosures have been limited to the interaction of Factor VIII with the enzyme Factor IXa. The non-activated proenzyme Factor IX, which may display significantly different binding requirements, has not been previously addressed.

SUMMARY OF THE INVENTION

This invention provides a peptide having an amino acid sequence derived from Factor VIII and being capable of binding to activated Factor IX and to its non-activated precursor.

Figure 2:
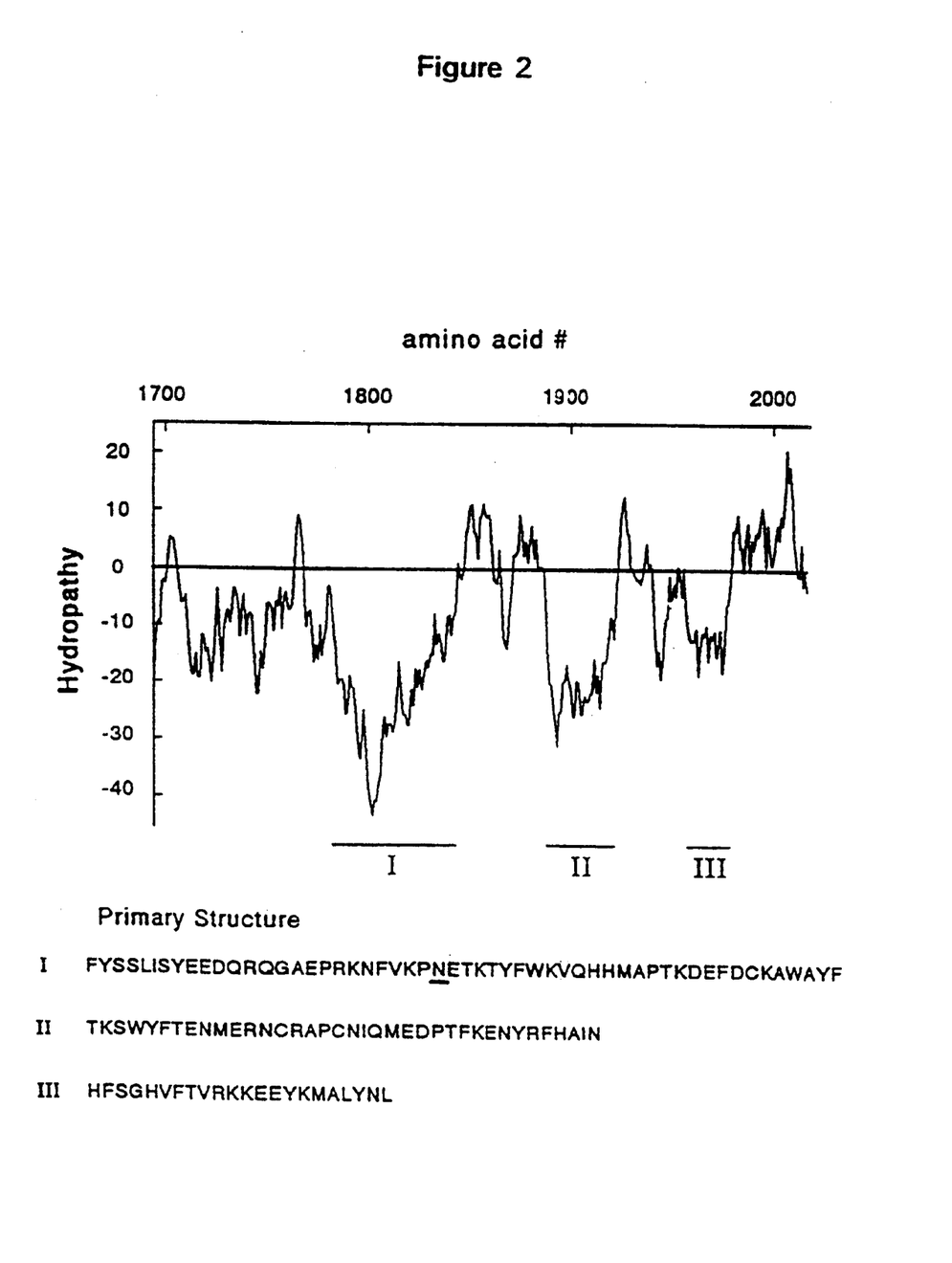

Said amino acid sequence is preferably derived from human Factor VIII. More specifically, said amino acid sequence is derived from an exosite of Factor VIII, in particular an exosite located in the A3-domain of Factor VIII, such as the exosite I of the human Factor VIII A3-domain as shown in FIG. 2 (SEQ ID NO: 13).

Preferably, said amino acid sequence comprises two basic amino acid residues separated by between 3 and 6 further amino acid residues, at least two of said further amino acid residues being selected from the group consisting of hydrophobic and aromatic amino acid residues. More preferably, said amino acid sequence comprises the sequence Glu-Thr-Lys-Thr-Tyr-Phe-Trp-Lys (SEQ ID NO: 1).

The peptide will generally have a length of from 8 to 200 amino acid residues, such as from 8 to about 150, preferably from 8 or 9 to 55, and most preferably from 10 to 20 amino acid residues.

According to a preferred embodiment of the invention, the peptide comprises 10 to 20 amino acid residues from the amino acid sequence Gly-Ala-Glu-Pro-Arg-Lys-Asn-Phe-Val-Lys-Pro-Asn-Glu-Thr-Lys-Thr-Tyr-Phe-Trp-Lys-Val-Gln-His-His-Met-Ala-Pro-Thr-Lys-Asp-Glu-Phe, (SEQ ID NO: 2) including the sequence Glu-Thr-Lys-Thr-Tyr-Phe-Trp-Lys (SEQ ID NO: 1).

According to another preferred embodiment of the invention, the peptide is a fragment of from 10 to 20 amino acids from the amino acid sequence Gly-Ala-Glu-Pro-Arg-Lys-sn-Phe-Val-Lys-Pro-Asn-Glu-Thr-Lys-Thr-Tyr-Phe-Trp-Lys-Val-Gln-His-His-Met-Ala-Pro-Thr-Lys-Asp-Glu-Phe, (SEQ ID NO: 2) said fragment comprising the sequence Glu-Thr-Lys-Thr-Tyr-Phe-Trp-Lys (SEQ ID NO: 1).

The subject invention furthermore provides a pharmaceutical composition comprising a peptide as defined herein and a pharmaceutically acceptable carrier or excipient. In particular, said pharmaceutical composition is for the treatment of thrombotic disorders and comprises the peptide(s) in an effective amount for inhibiting the intrinsic blood coagulation pathway.

The invention also provides a method of treatment of a mammal, in particular a human individual against thrombotic disorders comprising administering to said individual a peptide as defined herein in an effective amount for inhibiting the intrinsic blood coagulation pathway.

BRIEF DESCRIPTION OF THE DRAWINGS

FIG. 1 shows an overview of the mechanisms involved in thrombus formation. Vascular damage leads to the exposure of Tissue Factor, and triggers the activation of Factor X by the extrinsic pathway. In complex with activated Factor V, Factor Xa converts prothrombin into thrombin, the key enzyme in the haemostatic response. Thrombin induces primary thrombus formation by activating platelets and by converting fibrinogen into fibrin. After some initial delay, thrombin further activates the cofactors Factor V and Factor VIII, the latter being an essential cofactor in the intrinsic coagulation pathway. After activation of Factor IX by either Factor VIIa/Tissue Factor or by Factor XIa, this leads to the secondary haemostatic response by additional thrombin and Factor Xa formed by the Factor IXa/Factor VIIIa complex (indicated in bold) of the intrinsic pathway. This secondary mechanism is the target of the anticoagulant compounds of the present invention.

FIG. 2 shows a hydropathy plot of the Factor VIII A3-domain. The plot was constructed as described in Example I. The plot reveals the existence of three discrete regions with low hydropathy values, which reflect the hydrophilic nature associated with potentially exposed exosites (SEQ ID NOS: 13–15). These are indicated as I, II and III (SEQ ID NOS: 13–15). The primary structure of these exosites is also listed. The primary sequence of these exosites is also listed. Exosite I further contains a site for N-linked glycosylation (Asn at position 1810, see G. A. Vehar et al., *Nature* vol 312, 1984, pp 337–342). This position within exosite I is underlined (N).

FIG. 5 shows the effect of a synthetic Factor IX binding peptide on the haemostatic system. The compound KNFVKPNETKTYFWK (SEQ ID NO: 3) was tested in standard tests for the intrinsic (APTT) and extrinsic (PT) coagulation pathway as described in Example VII. Tests were performed using human (panel A or FIG. 5A) and rabbit (panel B or FIG. 5B) plasma. The data show that the Factor IX binding compound KNFVKPNETKTYFWK (SEQ ID NO: 3) inhibits in the intrinsic coagulation pathway, while leaving the extrinsic coagulation pathways unaffected.

DETAILED DESCRIPTION OF THE PREFERRED EMBODIMENTS

The present invention relates to biologically active peptides which specifically inhibit the Factor IX-dependent pathway of blood coagulation. Said peptides exert inhibitory function because they comprise a motif involved in binding to activated Factor IX or its non-activated precursor, thereby competing with Factor VIII. Said peptides are based on a specific motif derived from one or more exosites within the amino acid sequence of Factor VIII.

The term "exosite" is used herein in a broad sense, and refers to relatively hydrophilic parts of the protein which are likely to be oriented towards the surface of the Factor VIII molecule. The term "motif" refers herein to a typical sequence pattern of hydrophilic and hydrophobic amino acids, including natural and synthetic analogues thereof, which comprise the minimal requirements for binding of activated or non-activated Factor IX. The term "Factor IX" is used herein to refer to blood coagulation Factor IX, including both activated and non-activated forms thereof.

The term "derived from" is used herein to refer primarily to a sequence occurring in the Factor VIII sequence, but it also encompasses modified sequences having similar or even improved characteristics with respect to binding of activated and/or non-activated Factor IX. Usually, said modification will consist of a substitution of a limited number of amino acid residues, say at most 20%, preferably at most 10% of the amino acid residues, by other amino acid residues, usually of the same category (hydrophobic amino acids being replaced by other hydrophobic amino acids, basic amino acids by other basic amino acids, etc.). Amino acid additions and deletions, however, are also intended to be encompassed by the term "modification". Said term furthermore embraces multimeric forms of the peptide, such as e.g. tandem repeats. Chemical modifications of particular amino acids are also embraced, especially chemical modifications of the N-terminal and/or C-terminal amino acid residues, such as blocking of the terminal amino and/or carboxy groups, or the attachment of a molecule or moiety having a function, such as a carrier function, a targeting function, etc. The term "modification" further embraces the addition or removal of glycosyl-residues which may modulate the exposure of the Factor IX binding motif.

In a first set of particularly preferred embodiments of the subject invention, the peptide is derived from one or more of the exosites within the sequence of the Factor VIII molecule, preferably of the Factor VIII light chain, and more preferably of the Factor VIII A3-domain. Furthermore, although the invention covers peptides based on exosites of Factor VIII from any mammalian species, said peptides are preferably derived from the sequence of human Factor VIII.

According to another set of particularly preferred embodiments, the peptides of this invention comprise a motif consisting of a repeat of at least two basic amino acid residues (Lys, Arg, or analogues thereof), separated by a cluster of amino acids that is relatively rich in hydrophobic or aromatic amino acids, or analogues thereof. More preferably, the motif consists of two basic amino acid residues separated by between 3 and 6 other residues, the majority of which being hydrophobic or aromatic. Most preferably, the peptide comprises the motif ETKTYFWK (SEQ ID NO: 1) (Glu-Thr-Lys-Thr-Tyr-Phe-Trp-Lys (SEQ ID NO: 1)), which corresponds to the residues 1811–1818 of the human Factor VIII A3-domain.

In another particularly preferred embodiment, the peptide comprising the Factor IX-binding motif represents a fragment of the Factor VIII light chain. This may be obtained from the intact Factor VIII heterodimer by dissociating the heavy and light chain, and isolating the light chain by methods well known in the art, for instance by immunoaffinity chromatography employing an antibody against one of the exosites on the Factor VIII A3-domain. In particular, the peptide may consist of a proteolytic fragment of the Factor VIII light chain, more preferably of the Factor VIII A3-domain. Such fragments may be produced by methods known to the average expert in the art, for instance by digestion with proteolytic enzymes such as chymotrypsin, trypsin and the like. The enzymatic digestion may further comprise incubation with appropriate glycosidases to specifically remove oligosaccharides from the glycosylation sites, including that at residue 1810 in the A3-domain. Peptides containing the Factor IX binding motif then can be isolated by standard immunoaffinity chromatography techniques, employing an antibody with its epitope near or at the Factor IX-binding motif.

In another particularly preferred embodiment, the Factor IX-binding motif containing peptide is obtained by recombinant DNA techniques, in which DNA encoding part of the Factor VIII light chain or, more preferably, of the Factor VIII A3-domain or part thereof, is introduced into an appropriate plasmid for in vitro translation or for expression in prokaryotic or eukaryotic host cells, or for expression in biological fluids, including milk, of transgenic animals. One skilled in the art will easily identify appropriate methods to achieve this. The DNA encoding the Factor IX-binding peptide may contain various mutations within the Factor IX-binding motif (see above), or in the proximity thereof, for instance at the Asn residue that represents the glycosylation site within the Factor VIII A3-domain (see FIG. 2). The expressed peptides can further be modified by the same enzymatic methods as described above for obtaining fragments of the Factor VIII light chain. The expressed peptides can be purified by the same immunoaffinity chromatography approach as specified above for protein fragments generated by limited proteolysis.

Compounds of the present invention may also be produced by standard peptide synthesis techniques. Oligopeptides which comprise the Factor IX-binding motif may be coupled to carrier proteins including albumin or other plasma proteins to prolong half-live of the peptide in the recipient's circulation.

The compounds disclosed in the present invention may be formulated for administration in any convenient way, and the invention includes within its scope pharmaceutical compositions containing a therapeutically effective amount of at least one peptide comprising the Factor IX-binding motif. Such compositions may be formulated in a conventional manner using one or more pharmaceutically acceptable carriers or excipients. Suitable carriers include, but are not limited to, diluents or fillers, sterile aqueous media nd various non-toxic organic solvents. The compositions may be formulated in the form of tablets, capsules, powders, aqueous suspensions or solutions, injectable solutions and the like. Appropriate dosage forms may be easily identified by a person skilled in the art.

The method of this invention should preferably be carried out employing a dosage regimen which ensures maximum therapeutic response until improvement is achieved, and thereafter the minimum effective level which gives appropriate protection against thrombosis. In general, the dose will be dependent on the molecular size of the peptide used. For an oligopeptide of about 15 amino acids, the dosage for intravenous administration may vary between approximately 0.1 and 1000 mg/kg, preferably between 1 and 500 mg/kg, and most preferably between 10 and 100 mg/kg. For larger peptides, the dose may be increased accordingly. For oral administration, the dose may be substantially higher, bearing in mind, of course, that appropriate dosage may also be dependent on the patient's general health, age and other factors which may influence the response to the drug. The drug may be administered by continuous infusion, or at regular intervals of approximately 4 to 50 hours to maintain the therapeutic effect at the desired level.

The invention is illustrated in the subsequently described Examples. While exemplary of the present invention as applied to the identification, preparation and use of anticoagulant peptides derived from the Factor VIII light chain, the invention is construed to be applicable to the Factor VIII heavy chain as well. Variations within the purview of one skilled in the art are to be considered to fall within the scope of the present invention. Unless defined otherwise, all technical and scientific terms used herein have the same meaning as commonly understood by one of ordinary skill in the art to which this invention belongs. Although any methods and materials similar or equivalent to those describes herein can be used in the practice or testing of the present invention, the preferred methods and materials are now described.

EXAMPLE I

Identification of Potentially Factor IXa Binding Exosites within the Factor VIII A3-domain A simple method for the identification of exosites potentially involved in protein-protein interaction has been previously established (J. Kyte and R. F. Doolittle, *J. Mol. Biol.* vol 157, 1982, pp 105–132). This method provides a program that progressively evaluates the hydrophilicity and hydrophobicity of a protein along its amino acid sequence. The method employs a hydropathy scale which reflects the average hydropathy within segments of predetermined size along the amino acid sequence. Hydrophilic sections are characterised by negative hydropathy values, and are likely candidates to be oriented towards the exterior of a protein which is in an aqueous solution. We have applied this method to the known sequence of human Factor VIII (G. A. Vehar et al., *Nature* vol 312, 1984, pp 337–342; J. J. Toole et al., *Nature* vol 312, 1984, 342–347), employing a segment size ("window") of 19 residues. From the complete sequence of Factor VIII the region 1689–2019, which corresponds with the Factor VIII A3-domain, was selected for this analysis, and the resulting hydropathy plot is shown in FIG. 2. This method revealed three discrete regions with low hydropathy values, which reflect the hydrophilic nature associated with potential exosites. These are indicated as exosite I, II and III in FIG. 2, (SEQ ID NOS: 13–15) and encompass the Factor VIII amino acid residues 1785–1839, 1887–1923 and 1957–1979, respectively. The primary structure of these exosites is also given in FIG. 2. Although this method employs principles that have long been appreciated in the art, and is based on the Factor VIII sequence as previously published, these hydrophilic exosites have previously received virtually no attention. Among the potential interactive sites, exosite I (SEQ ID NO: 13) is particularly striking by its extremely low hydropathy index.

EXAMPLE II

Synthesis of Peptides that Represent a Major Exosite of the Factor VIII A3-domain From the three major exosites of the Factor VIII A3-domain, exosite I was selected for more detailed evaluation of Factor IXa and Factor IX binding. This exosite comprises the Factor VIII residues 1785–1839, the sequence of which is summarized in FIG. 2. From this sequence a number of partially overlapping peptides were selected which an approximate length of 10 to 20 amino acids. Such oligopeptides can be synthesized by a variety of methods that are well known in the art. We employed an established method, the so-called "T-bag method" (R. A. Houghtony, *Proc. Natl. Acad. Sci. U.S.A.* vol 82, 1985, pp 5131–5135) and standard N-9-fluorenylmethoxycarbonyl (Fmoc) chemistry (W. van't Hof et al., *Mol. Immunol.* vol 28, 1991, pp 1225–1232). Briefly, the first Fmoc-protected amino acid was coupled to a p-benzyloxybenzyl alcohol resin (S. S. Wang, *J. Am. Chem. Soc.* vol 95, 1973, pp2328–1333) and sealed into a 64 μm mesh polypropylene T-bag. Coupling reactions were performed in N,N-dimethylformamide using a 10-fold excess of N-Fmoc-protected amino acid over the first immobilized amino acid, a 10-fold excess of 1-hydroxybenzotriazole to suppress racemization, and a 13-fold excess of N,N-diisopropylethylamine. Deprotection was performed with 30% piperidine in N,N-dimethylformamide. Resins and amino acids were obtained from Novabiochem (Laufelfingen, Switzerland) and solvents were from Merck (Darmstadt, Germany). Semipermanent side chain protection of Arg, His and Cys was achieved by appropriate reagents as described (W. van't Hof et al., *Mol. Immunol.* vol 28, 1991, pp 1225–1232). After the final coupling, trifluoracetic acid containing 5% thioanisole was employed for side chain deprotection and simultaneous release of peptides from the solid support. Finally, peptides were extracted and lyophilized. By using this method, a series of overlapping peptides was synthesized covering the sequence of exosite I of the Factor VIII A3-domain (see FIG. 2).

A selection of these peptides will be further characterized below (see Example III). This includes the compounds YSSLISYEEDQGAE (SEQ ID NO: 4), GAEPRKNFVKP-NETK (SEQ ID NO: 5), KNFVKPNETKTYFWK (SEQ ID NO: 3), ETKTYFWKVQ (SEQ ID NO: 7), YFWKVQHH-MAPTKDEFDCKA (SEQ ID NO: 8), and HMAPTK-DEFDCKA (SEQ ID NO: 9), which correspond with the Factor VIII A3-domain regions 1786–1801, 1799–1813, 1804–1818, 1811–1820, 1815–1834, and 1822–1834, respectively.

EXAMPLE III

Identification of a Factor IXa Binding Motif on the Factor VIII A3 Domain

Figure 3:
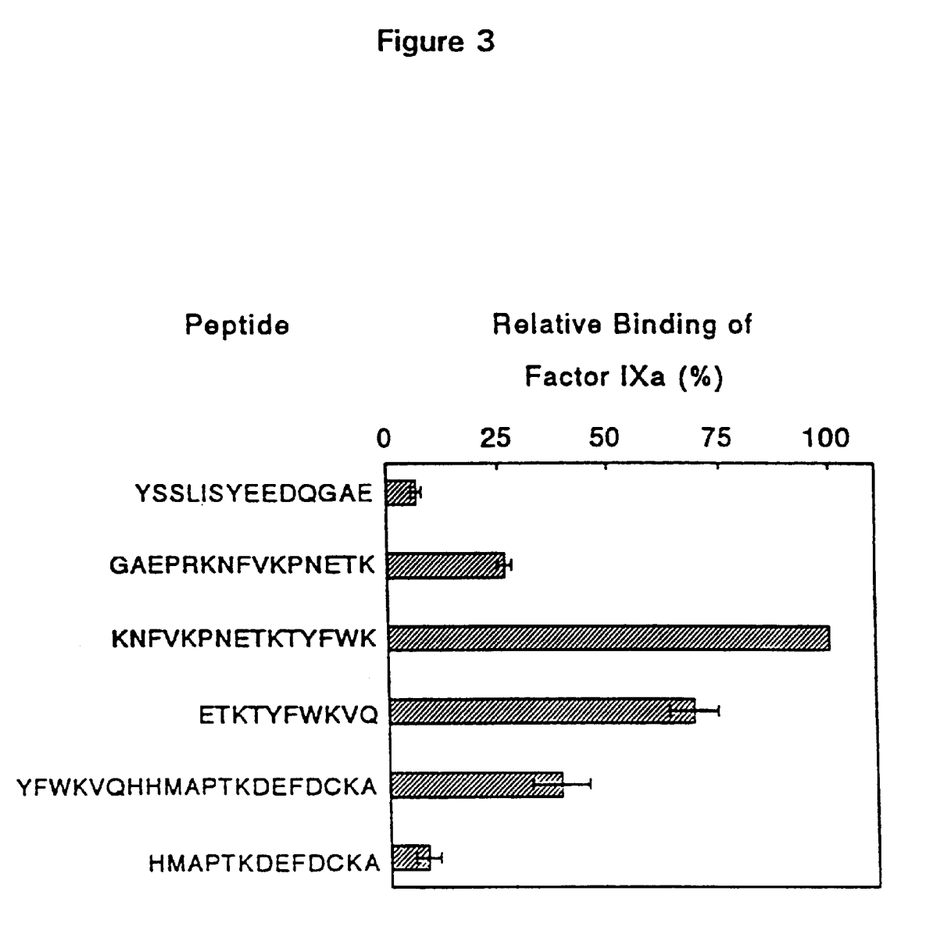
FIG. 3 summarizes the identification of a Factor IXa binding site on the Factor VIII A3 domain employing a series of partially overlapping peptides (SEQ ID NOS: 4,5,7,8 and 9). The peptides were synthesized employing the method described in Example II. Factor IXa binding was assessed as described in Example III.

The synthetic peptides described in Example II were examined for Factor IXa binding employing a standard ELISA-derived technique. Peptides were immobilized on regular microtiter plates (Immulon, Dynatech, Plockingen, Germany) in an amount of 0.8 nmol of peptide per well. Remaining binding sites were blocked using 2% (w/v) of human serum albumin in a buffer containing 0.1% (v/v) Tween-20, 0.1M NaCl and 25 mM Tris (pH 7.4). After washing, the immobilized peptides were incubated for 1 hour at 37° C. with 100 μl of the same buffer containing 50 nM of purified human Factor IXa (K. Mertens and R. M. Bertina, *Thromb. Haemostasis* vol 47, 1982, pp 96–100). After washing, wells were incubated with an appropriate amount of anti-human Factor IX antibody conjugated to horseradish peroxidase by the method of Nakane et al. (*J. Histochem. Cytochem.* vol 22, 1974, pp 1084–1091). Finally bound Factor IXa was detected using the substrate 3-3'-5-5'-tetramethylbenzidine, by reading the absorbance at 450 nm. FIG. 3 displays the results obtained using the selected oligopeptides from the Factor VIII light chain. The results show that the strategy of using overlapping synthetic segments along the amino acid sequence successfully identified a Factor IXa binding site within exosite I of the A3-domain. Two peptides proved particularly effective in Factor IXa binding: compounds KNFVKPNETKTYFWK (SEQ ID NO: 3) and ETKTYFWKVQ (SEQ ID NO: 7), which are corresponding with the Factor VIII residues 1804–1818 and 1811–1820, respectively. The finding that these two compounds share the same Factor IXa binding properties implies that the overlapping sequence ETKTYFWK (SEQ ID NO: 1) meets the minimal requirements for Factor IXa binding, and as such may be regarded as a Factor IXa binding motif.

EXAMPLE IV

Figure 4:
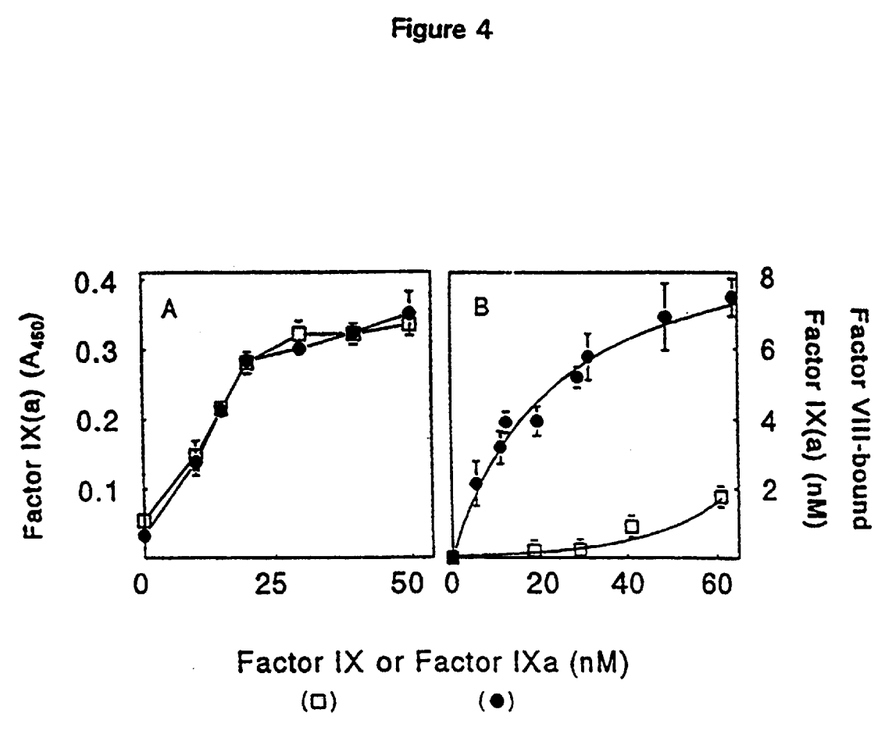
FIG. 4, displays the interaction of Factor IXa (closed symbols) or non-activated Factor IX (open symbols) with an immobilized synthetic peptide (panel A or FIG. 4A) and with the immobilized complete Factor VIII light chain (panel B or FIG. 4B). Details are provided in Example IV. Comparison of Panels A and B (FIGS. 4A and B) demonstrates that the synthetic peptide does not distinguish between Factor IXa and non-activated Factor IX, whereas the complete Factor VIII light chain displays strong preference for binding to the activated form, Factor IXa.

Interaction of Peptides Comprising the Factor IXa Binding Motif with Activated and Non-Activated Factor IX The same immobilized synthetic oligopeptides may be used for examining the interaction with the non-activated Factor IX zymogen rather than with Factor IXa (see Example III). For this purpose, we selected the compound KNFVKPNETKTYFWK (SEQ ID NO: 3) as an example of an oligopeptide that comprises the Factor IXa binding motif ETKTYFWK (SEQ ID NO: 1), and compared this compound with the complete Factor VIII light chain, which contains this motif as well. The experimental conditions were as described for Factor IXa binding to oligopeptides (see Example III) or to the complete Factor VIII light chain polypeptide (see P. J. Lenting et al., *J. Biol. Chem.* vol 269, 1994, pp 7150–7155). Factor IXa was compared with a preparation of non-activated Factor IX which was completely devoid of Factor IXa (K. Mertens and J. A. van Mourik, International Patent ApDlication, WO 94/05692, published Mar. 17, 1994). The results of these experiments are shown in FIG. 4. A surprising parallel was observed between Factor IX and Factor IXa with respect to binding to the ETKTYFWK (SEQ ID NO: 1)-motif containing oligopeptide (FIG. 4A), but not to the complete Factor VIII light chain (FIG. 4B). The dissociation constant ($K_d$) of the complex between Factor IXa and the complete Factor VIII light chain region 1649–2332, or its cleaved derivatives encompassing residues 1690–2332 or 1722–2332, has previously been established to be 15 nM (see M. J. S. H. Donath et al., *J. Biol. Chem.* vol 270, 1995, pp 3648–3655), and it is evident from FIG. 4B that for non-activated Factor IX the Kd is significantly higher. For the compound KNFVKPNETKTYFWK (SEQ ID NO: 3) binding of Factor IX and Factor IXa were compared in more detail by equilibrium binding studies. For this purpose, Factors IX or IXa (30 nM) were incubated with varying concentrations (0.2–0.6 $\mu$M) of compound KNFVKPNETKTYFWK (SEQ ID NO: 3) in a buffer containing 2% (w/v) of human serum albumin, 0.1% (v/v) Tween-20, 0.1M NaCl and 25 mM Tris (pH 7.4). After incubation for 16 h at room temperature, the amount of non-bound Factor IXa or Factor IX was determined by incubating samples in microtiter wells containing the immobilized peptide compound. Non-bound Factor IX or Factor IXa then was allowed to bind to the immobilized peptide, and subsequently quantified employing a peroxidase-conjugated antibody against Factor IX, as described in detail in the Example III. This method has been well established in the art (B. Friguet et al., *J. Immunol. Methods* vol 77, 1985, 305–319), and provides the dissociation constant Kd by the expression:

$$A_o/(A_o-A)=1+K_d/c$$

wherein $A_o$ represents the absorbance in the absence of peptide in the original solution, A is the absorbance in the presence of peptide, and c is the concentration of peptide employed. By this method, $K_d$ values for binding of compound KNFVKPNETKTYFWK (SEQ ID NO: 3) to Factor IXa and Factor IX were calculated to be 0.20±0.02 mM and 0.23±0.02 mM, respectively (mean±standard deviation). This demonstrates that, in contrast to the complete Factor VIII light chain, fragments thereof which comprise the Factor IXa binding motif of the A3-domain may no longer distinguish between activated and non-activated Factor IX.

EXAMPLE V

Preparation of Peptides Comprising the Factor IX Binding Motif by Enzymatic Digestion of the Factor VIII Light Chain The complete Factor VIII light chain (residues 1648–2332, see G. A. Vehar et al., *Nature* vol 312, 1984, pp 337–342) may be subjected to enzymatic digestion in order to generate fragments comprising the Factor IX binding motif. A variety of enzymes may be useful for this purpose, as will be evident from the description given below.

First, the amino-terminal portion of the Factor VIII light chain may be cleaved off using thrombin or Factor Xa. These enzymes cleave between residues 1689 and 1690, or 1721 and 1722, respectively (G. A. Vehar et al., *Nature* vol 312, 1984, pp 337–342). Methods to achieve this have been previously described in full detail (Donath et al., *J. Biol. Chem.* vol 270, 1995, pp 3648–3655) and will be easily reproduced by an average expert in the art. Briefly, purified Factor VIII light chain (310 nM) was incubated either with thrombin (20 nM) or with a combination of Factor Xa (20 nM) and phospholipids (25 $\mu$M), in a buffer containing 100 mM NaCl, 10 mM $CaCl_2$, 50 mM Tris (pH 7.4). After incubation for 45 min at 37° C., the reaction was terminated by adding a synthetic chloromethyl ketone inhibitor of thrombin or Factor Xa at a final concentration of 30 nM, and cleaved Factor VIII light chain was purified by immunoaffinity chromatography as described (see Donath et al., *J. Biol. Chem.* vol 270, 1995, pp 3648–3655).

Second, purified Factor VIII light chain (see Lenting et al., *J. Biol. Chem.* vol 269, 1994, pp 7150–7155) was subjected to enzymatic digestion by a glycosidase in order to remove N-linked glycosyl residues, in particular those on the Asn residue at position 1810 (see G. A. Vehar et al., *Nature* vol 312, 1984, pp 337–342). To achieve this, Factor VIII light chain (0.4 mg/ml) was incubated with the enzyme Peptide-$N^4$-(N-acetyl-$\beta$-glucosaminyl) asparagine amidase (EC 3.5.1.52, obtained as N-Glycanase from Sanbio BV, Uden, The Netherlands) at a final concentration of 10 U/ml in 3 mM EDTA, 0.1 M phosphate (pH 7.8) for 16 hours at 37° C. After incubation, the reaction mixture was analysed by SDS-polyacrylamide gel electrophoresis as described in detail previously (see Donath et al., *J. Biol. Chem.* vol 270, 1995, pp 3648–3655). The enzymatic deglycosylation was apparent from a decrease in molecular size by approximately 8 kDa.

Third, the purified Factor VIII light chain was converted into smaller fragments using the enzyme Lysyl endopeptidase (EC 4.21.50, obtained from Sopar Biochem, Lunteren, The Netherlands). Factor VIII light chain (100 $\mu$g/ml) was incubated with Lysyl endopeptidase (6.6 $\mu$g/ml) in a buffer containing 4.5% (v/v) glycerol, 150 mM NaCl, 50 mM Tris (pH 7.8) at 37° C. After various incubation times, samples of the reaction mixture were withdrawn for analysis by SDS-polyacrylamide gel electro-phoresis. During the initial phase of the reaction, the 80 kDa Factor VIII light chain was converted into components of between 30 and 40 kDa. Upon more prolonged incubation, these fragments were further degraded, until a major component of 17 kDa accumulated after 1 hour of incubation. These conditions served for the digestion of Factor VIII light chain on a preparative scale. After 1 hour of incubation, the reaction was terminated by adding the synthetic endopeptidase inhibitor Pefabloc SC (Pentapharm, Basel, Switzerland) to a final concentration of 1 mM. Factor VIII peptides containing the Factor IX binding motif then were isolated by immunoaffinity chromatography employing the monoclonal antibody CLB-CAg A, which is directed against residues 1801–1823 within the Factor VIII A3-domain (J. W. van de Loo et al., Annual Report 1992, Dr. Karl Landsteiner Foundation, Amsterdam, p 1), thus including the Factor IX binding motif ETKTYFWK (SEQ ID NO: 1) within exosite I (SEQ ID NO: 13) (FIG. 2). The antibody CLB-CAg A was immobilized on CNBr-activated Sepharose 4B (Pharmacia, Stockholm, Sweden) at a density of 1 mg/ml gel. The column was equilibrated with a buffer containing 2% (v/v) glycerol, 100 mM NaCl, 50 mM Tris (pH 7.8). After equilibration, the Factor VIII light chain digest was applied and the column was extensively washed with equilibration buffer. Subsequently, bound protein was eluted in 55% (v/v) ethylene glycol, 100 mM NaCl, 25 mM lysine (pH 11.0), and the eluate was immediately neutralized by collection in 1/5 volume of 1 M imidazole (pH 7.0). Analysis of the eluted protein by SDS-polyacrylamide gel electrophoresis revealed that it consisted predominantly of the 17 kDa fragment. This A3-domain fragment, which comprises the antibody epitope within exosite I (SEQ ID NO: 13) (residues 1801–1823, see above) was further characterized with respect to its anticoagulant properties as described below (see Example VII).

Collectively, these digestion experiments demonstrate that a variety of methods may be used to convert the Factor VIII light chain into smaller peptides which still comprise exosite I (SEQ ID NO: 13) of the A3-domain, while being separated from other parts of the Factor VIII light chain or from glycosylated moieties contained therein.

EXAMPLE VI

Preparation of Recombinant Peptides Comprising the Factor IX Binding Motif

Peptides comprising the Factor IX binding motif may also be prepared by a variety of recombinant DNA techniques, in which DNA encoding the desired peptide is introduced into an appropriate expression plasmid. The present example describes in vitro expression of recombinant peptides in a reticulocyte lysate, but similar techniques for expression of the same peptides in other in vitro expression systems or in prokaryotic or eukaryotic host cells will be easily identified by the average expert in the art. In vitro transcription and translation was performed employing the SP6 expression system and the plasmid pSP64 (Promega Corporation, Leiden, the Netherlands). The previously described plasmid pSP/F8-80K1 (A. Leyte et al., *Biochem. J.* vol 263, 1989, pp 187–194) was used as a template for the construction of a truncated Factor VIII fragment employing the polymerase chain reaction (PCR). The DNA fragment was made by using the sense primer 5'-ACG ATT TAG GTG ACA CTA TAG-3' (SEQ ID NO: 10) (containing a part of the SP6 promotor) in combination with the anti-sense primer 5'-TTA GGA TCC TCA CAT ATG ATG TTG CAC TTT-3' (SEQ ID NO: 11). PCR-reactions of this primer combination yielded the Factor VIII DNA sequence between basepairs 4744 and 5526, which encodes for the Factor VIII residues from 1563 to 1823. The anti-sense primer enclosed a BamHI-restriction site (underlined) and a stop-codon (bold). The sense-primer was designed to contain a HindIII-restriction site at the 5'-terminus after PCR. After digestion of the PCR product and plasmid pSP64 with HindIII and BamHI, the product was ligated into the plasmid. This Factor VIII construct then was transcribed and translated employing the SP6-expression system according to the manufacturer's standard protocol. After translation, the produced peptides were incubated with the immobilized monoclonal antibody CLB-CAg A as specified in detail in Example V. After extensive washing, one major peptide of approximately 30 kDa was eluted.

The eluted recombinant peptide was dialysed into a buffer containing 4.5% (v/v) glycerol, 100 mM NaCl, 10 mM CaCl$_2$, 50 mM Tris (pH 7.4), and subjected to proteolytic digestion at the thrombin cleavage site between the Factor VIII residues 1689 and 1690 (M. J. S. H. Donath et al., *J. Biol. Chem.* vol 270, 1995, pp 3648–3655). The recombinant peptide was incubated with thrombin under the same conditions as specified for the complete Factor VIII light chain in Example V. After incubation for 45 min at 37° C., the reaction was terminated as described above, and the reaction mixture was subjected to a second immunnoaffinity chromatography using the immobilized antibody CLB-CAg A as specified in Example V. After elution, a peptide was obtained of approximately 17 kDa. This is consistent with a protein which comprises the Factor VIII residues 1690–1823, including the epitope of antibody CLB-CAg A in exosite I of the Factor VIII A3-domain.

EXAMPLE VII

Effect of Factor IX Binding Peptides on the Haemostatic System

Figure 5:
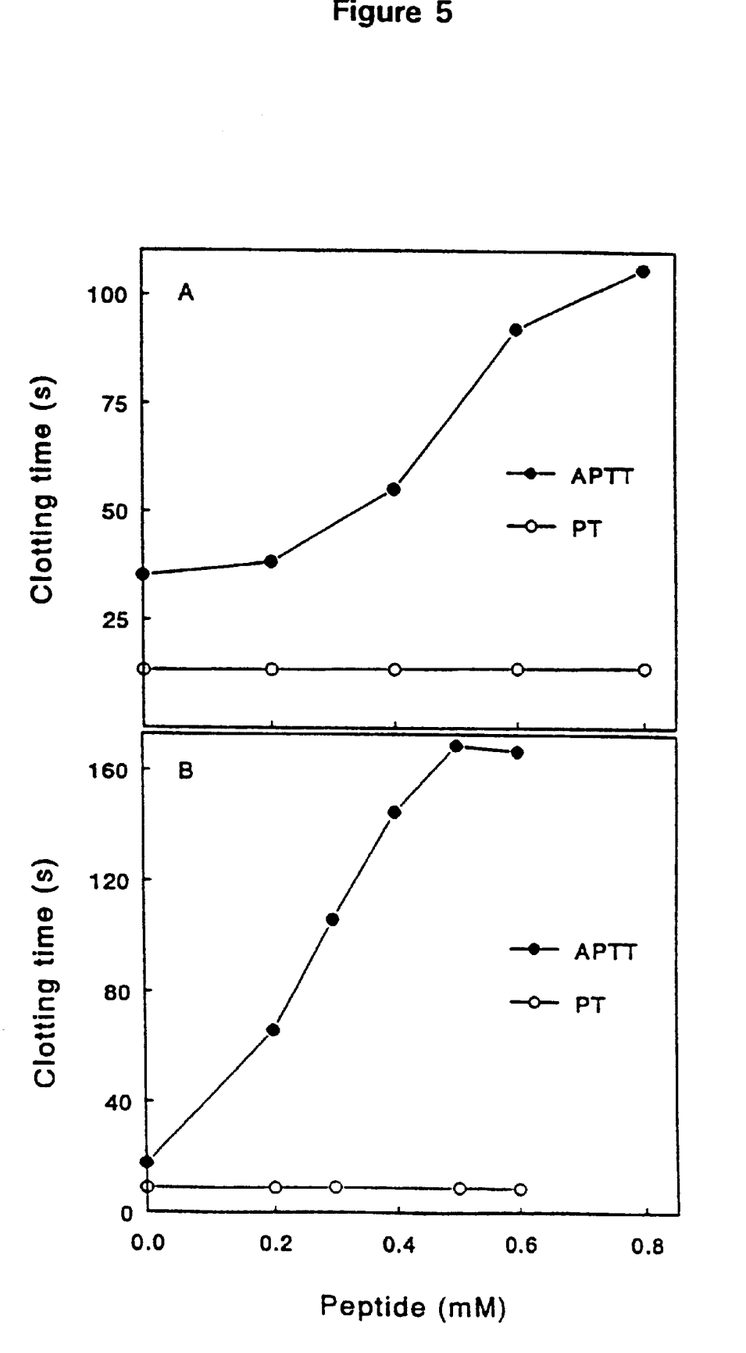

If the interaction of Factor VIII-derived peptides with Factor IX or Factor IXa were representing a physiologically significant process, similar concentrations of the same components should also effectively inhibit the coagulation cascade as a whole. Moreover, if inhibition would occur, it should be specifically limited to the intrinsic coagulation pathway (cf. FIG. 1). The established art in the field of haematology provides simple laboratory tests to assess the physiological status of the intrinsic and extrinsic coagulation pathway. The former is known in the art as the APTT test ("Activated Partial Thromboplastin Time"), and the latter as the PT test ("Prothrombin Time"). To assess the effect of Factor VIII-derived peptides on the coagulation system, these compounds were tested for their effect in the established PT and APTT methods (R. Biggs, *Human Blood Coagulation Haemotasis and Thrombosis*, 2nd edition, Blackwell, Oxford, 1976, pp 310–364). The APTT test was performed as follows: in a plastic test tube, 400 μl of human citrated, platelet-poor plasma were mixed with 40 μl of a solution of Factor VIII light chain or compound KNFVK-PNETKTYFWK (SEQ ID NO: 3) in a buffer containing 0.1 M NaCl and 25 mM Tris (pH 7.4). After pre-incubation for 15 min at 37° C., 100 μl of this mixture were mixed with 100 μl of a commercial APTT reagent (Baxter-Dade, Düdingen, Switzerland) containing phospholipids and colloidal silica to activate the contact system of coagulation (cf. FIG. 1). After 3 min then 100 μl of a prewarmed 0.33 M CaCl$_2$ solution were added, and the clotting time was recorded. For the PT test, 400 μl of plasma and 40 μl of Factor VIII peptide solution were incubated for 15 min at 37° C. Subsequently, 200 μl of this mixture were mixed with 200 μl of a pre-warmed commercial PT reagent (Thromborel-S, Behring, Marburg, Germany), and the clotting time was recorded. As shown in FIG. 5A, compound KNFVKPNET-KTYFWK (SEQ ID NO: 3) proved particular effective in inhibiting the APTT test, whereas the PT test remained completely unaffected. This demonstrates that compound KNFVKPNETKTYFWK (SEQ ID NO: 3) specifically inhibits the intrinsic coagulation pathway (cf. FIG. 1). The extent of inhibition was even more pronounced when rabbit plasma was used instead of human plasma (FIG. 5B). In this case, the APTT was 5-fold prolonged, which seems at least as significant as the effect of other antithrombotic agents, including heparin and hirudin, in another rodent model (P. Klement et al., *Thromb. Haemostasis* vol 68, 1992, pp 64–68). Half-maximal inhibition occurred at approximately 0.3 mM (see FIG. 5). As expected, this value directly reflects the K$_d$ observed for the interaction of this compound with Factor IXa and Factor IX (see Example IV). The same assay system was used for the characterization of the peptides obtained by enzymatic digestion of the Factor VIII light chain as described in Example V. The results of these experiments are summarized in Table I.

TABLE I

Properties of various Factor VIII light chain derivatives. Anticoagulant activity in the APTT test is expressed by prolongation of the clotting time in seconds.

| Factor IX(a)-binding peptide | Concentration (mg/ml) | Anticoagulant activity (seconds) |
| --- | --- | --- |
| Factor VIII light chain | 0.03 | 8.6 |
| Thrombin-cleaved light chain | 0.03 | 15.7 |
| Deglycosylated light chain | 0.06 | 16.9 |
| Isolated 17 kDa fragment | 0.03 | 14.1 |

These data demonstrate that enzymatic digestion of the Factor VIII light chain enhances its anticoagulant activity to a significant extent. Peptides that comprise the Factor IX binding motif of the Factor VIII A3-domain thus provide a substantial improvement over the intact Factor VIII light chain with respect to inhibitory activity in the intrinsic coagulation pathway.

One limitation of the intact Factor VIII light chain is associated with its low affinity for the non-activated Factor IX zymogen compared to that for Factor IXa (FIG. 4B). This limitation is overcome by smaller peptide derivatives such as compounds KNFVKPNETKTYFWF (SEQ ID NO: 3) (see FIGS. 4A and 5). Thus, effective inhibition of the intrinsic coagulation pathway is preferably accomplished by compounds that do comprise the Factor IXa binding motif of the Factor VIII A3-domain, but also display substantial binding to non-activated Factor IX. By virtue of their unique specificity for the intrinsic coagulation pathway, the Factor IX binding peptides of the present invention have particular utility in pharmaceutical compositions for the treatment of thrombotic disorders.

One skilled in the art will readily appreciate that the present invention is well adapted to carry out the objects and obtain the ends and advantages mentioned, as well as those inherent therein. The compounds, methods and compositions described herein are presented as representative of the preferred embodiments. These are intended to be exemplary and not as limitations on the scope of the present invention. Modifications thereof and other uses will occur to those skilled in the art, and are to be included within the spirit of the invention and the scope of the appended claims.

What is claimed is:

1. A peptide consisting of 8–20 amino acids, wherein said peptide has within said 8–20 amino acids, a sequence of amino acids from Factor VIII, Glu-Thr-Lys-Thr-Tyr-Phe-Trp-Lys (SEQ ID NO: 1), or a sequence of amino acids from Factor VIII, Glu-Thr-Lys-Thr-Tyr-Phe-Trp-Lys (SEQ ID NO: 1) wherein one or more of the SEQ ID NO: 1 amino acids have been substituted with other amino acids, and which peptide of 8–20 amino acids binds to activated Factor IX and to its non-activated precursor.

2. The peptide of claim 1 wherein said peptide is from human Factor VIII.

3. The peptide of claim 1 wherein said amino acid sequence is from an exosite of Factor VIII.

4. The peptide of claim 1 wherein amino acid sequence is from an exosite located in the A3-domain of Factor VIII.

5. The peptide of claim 1 wherein said amino acid sequence is from exosite I of the human Factor VIII A3-domain as shown in SEQ ID NO.13.

6. The peptide of claim 1 wherein its length is from 10 to 20 amino acid residues.

7. The peptide of claim 1 which consists of 10 to 20 amino acid residues from the amino acid sequence Gly-Ala-Glu-Pro-Arg-Lys-Asn-Phe-Val-Lys-Pro-Asn-Glu-Thr-Lys-Thr-Tyr-Phe-Trp-Lys-Val-Gln-His-His-Met-Ala-Pro-Thr-Lys-Asp-Glu-Phe (SEQ ID NO: 2).

8. A peptide according to claim 1 wherein said peptide has 8–10 amino acids.

9. A peptide according to claim 1 wherein said peptide has 10 amino acids.

10. A peptide according to claim 1 having SEQ ID NO: 1.

11. A peptide according to claim 1 wherein the number of substitutions of amino acids that have been substituted with other amino acids is at most 20%.

12. A peptide according to claim 1 wherein the number of substitutions of amino acids that have been substituted with other amino acids is at most 10%.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 8 amino acids
      (B) TYPE: amino acid
      (C) STRANDEDNESS: unknown
      (D) TOPOLOGY: unknown    (ii) MOLECULE TYPE: peptide    (iii) HYPOTHETICAL: NO    (xi) SEQUENCE DESCRIPTION: SEQ ID NO: 1:

Glu Thr Lys Thr Tyr Phe Trp Lys
1               5

(2) INFORMATION FOR SEQ ID NO: 2:

(i) SEQUENCE CHARACTERISTICS:
      (A) LENGTH: 32 amino acids
      (B) TYPE: amino acid
      (C) STRANDEDNESS: unknown
      (D) TOPOLOGY: unknown    (ii) MOLECULE TYPE: peptide    (iii) HYPOTHETICAL: NO    (xi) SEQUENCE DESCRIPTION: SEQ ID NO: 2:

Gly Ala Glu Pro Arg Lys Asn Phe Val Lys Pro Asn Glu Thr Lys Thr
1               5                   10                  15

Tyr Phe Trp Lys Val Gln His His Met Ala Pro Thr Lys Asp Glu Phe
                20                  25                  30

(2) INFORMATION FOR SEQ ID NO: 3:

(i) SEQUENCE CHARACTERISTICS:
      (A) LENGTH: 15 amino acids
      (B) TYPE: amino acid
      (C) STRANDEDNESS: unknown
      (D) TOPOLOGY: unknown    (ii) MOLECULE TYPE: peptide    (iii) HYPOTHETICAL: NO

```
    (xi) SEQUENCE DESCRIPTION: SEQ ID NO: 3:

Lys Asn Phe Val Lys Pro Asn Glu Thr Lys Thr Tyr Phe Trp Lys
1               5                   10                  15

(2) INFORMATION FOR SEQ ID NO: 4:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 4:

Tyr Ser Ser Leu Ile Ser Tyr Glu Glu Asp Gln Gly Ala Glu
1               5                   10

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 5:

Gly Ala Glu Pro Arg Lys Asn Phe Val Lys Pro Asn Glu Thr Lys
1               5                   10                  15

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 6:

Lys Asn Phe Val Lys Pro Asn Glu Thr Lys Thr Tyr Phe Trp Lys
1               5                   10                  15

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 7:

Glu Thr Lys Thr Tyr Phe Trp Lys Val Gln
1               5                   10

(2) INFORMATION FOR SEQ ID NO: 8:
```

(i) SEQUENCE CHARACTERISTICS:
    (A) LENGTH: 21 amino acids
    (B) TYPE: amino acid
    (C) STRANDEDNESS: unknown
    (D) TOPOLOGY: unknown (ii) MOLECULE TYPE: peptide (iii) HYPOTHETICAL: NO (xi) SEQUENCE DESCRIPTION: SEQ ID NO: 8:

Tyr Phe Trp Lys Val Gln His His Met Ala Pro Thr Asp Lys Asp Glu
1               5                   10                  15

Phe Asp Cys Lys Ala
            20

(2) INFORMATION FOR SEQ ID NO: 9:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 9:

His Met Ala Pro Thr Asp Lys Asp Glu Phe Asp Cys Lys Ala
1               5                   10

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: other nucleic acid (iii) HYPOTHETICAL: NO (xi) SEQUENCE DESCRIPTION: SEQ ID NO: 10:

ACGATTTAGG TGACACTATA G                                          21

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: other nucleic acid (iii) HYPOTHETICAL: NO (xi) SEQUENCE DESCRIPTION: SEQ ID NO: 11:

TTAGGATCCT CACATATGAT GTTGCACTTT                                 30

(2) INFORMATION FOR SEQ ID NO: 12:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 12:

Lys Asn Phe Val Lys Pro Asn Glu Thr Lys Thr Tyr Phe Trp Phe
1               5                   10                  15

(2) INFORMATION FOR SEQ ID NO: 13:

(i) SEQUENCE CHARACTERISTICS:
        (A) LENGTH: 54 amino acids
        (B) TYPE: amino acid
        (C) STRANDEDNESS: unknown
        (D) TOPOLOGY: unknown (ii) MOLECULE TYPE: other nucleic acid (iii) HYPOTHETICAL: NO (xi) SEQUENCE DESCRIPTION: SEQ ID NO: 13:

Phe Tyr Ser Ser Leu Ile Ser Tyr Glu Glu Asp Gln Arg Gln Gly Ala
1               5                   10                  15

Glu Pro Arg Lys Asn Phe Val Lys Pro Asn Glu Thr Lys Thr Tyr Phe
            20                  25                  30

Trp Lys Val Gln His His Met Ala Pro Thr Lys Asp Glu Phe Asp Cys
        35                  40                  45

Lys Ala Trp Ala Tyr Phe
    50

(2) INFORMATION FOR SEQ ID NO: 14:

(i) SEQUENCE CHARACTERISTICS:
        (A) LENGTH: 37 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 14:

Thr Lys Ser Trp Tyr Phe Thr Glu Asn Met Glu Arg Asn Cys Arg Ala
1               5                   10                  15

Pro Cys Asn Ile Gln Met Glu Asp Pro Thr Phe Lys Glu Asn Tyr Arg
            20                  25                  30

Phe His Ala Ile Asn
        35

(2) INFORMATION FOR SEQ ID NO: 15:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 15:

-continued

```
His Phe Ser Gly His Val Phe Thr Val Arg Lys Lys Glu Glu Tyr Lys
1               5                   10                  15

Met Ala Leu Tyr Asn Leu
                20
```